(12) United States Patent
Beasley

(10) Patent No.: US 7,113,162 B1
(45) Date of Patent: Sep. 26, 2006

(54) DIGITAL RADIOGRAPH ANALYZER AND METHODS

(75) Inventor: Bradley D. Beasley, 4526 E. P. True Pkwy., Apt. 108, West Des Moines, IA (US) 50265

(73) Assignee: Bradley D. Beasley, Broken Arrow, OK (US)

( * ) Notice: Subject to any disclaimer, the term of this patent is extended or adjusted under 35 U.S.C. 154(b) by 0 days.

(21) Appl. No.: 09/569,410

(22) Filed: May 12, 2000

(51) Int. Cl.
G09G 3/36 (2006.01)

(52) U.S. Cl. ............. 345/102; 345/162; 348/362; 378/165

(58) Field of Classification Search ........... 345/157, 345/164, 160, 166, 179, 173, 472.3, 102, 345/162, 569; 382/132, 154, 140; 378/162, 378/163, 164, 165, 166, 146, 4, 21, 98; 600/410, 600/411; 361/686, 683; 178/681, 19.01, 178/18.08, 18.03, 18.01, 18.02; 352/26; 348/362, 363, 364; 362/26

See application file for complete search history.

(56) References Cited

U.S. PATENT DOCUMENTS

| | | | | |
|---|---|---|---|---|
| 4,160,906 A | * | 7/1979 | Daniels et al. | 378/79 |
| 4,451,698 A | * | 5/1984 | Whetstone et al. | 178/18.07 |
| 4,943,689 A | * | 7/1990 | Siefer et al. | 178/18.11 |
| 5,028,744 A | * | 7/1991 | Purcell et al. | 178/18.11 |
| 5,084,908 A | * | 1/1992 | Alberici et al. | 378/4 |
| 5,098,383 A | * | 3/1992 | Hemmy et al. | 604/116 |
| 5,329,625 A | * | 7/1994 | Kannan et al. | 345/173 |
| 5,499,284 A | * | 3/1996 | Pellegrino et al. | 378/198 |
| 5,627,907 A | * | 5/1997 | Gur et al. | 382/132 |
| 5,740,267 A | * | 4/1998 | Echerer et al. | 382/132 |
| 5,779,634 A | * | 7/1998 | Ema et al. | 600/407 |
| 5,822,544 A | * | 10/1998 | Chaco et al. | 705/2 |
| 5,832,422 A | | 11/1998 | Wiedenhoefer | 702/154 |
| 6,311,419 B1 | * | 11/2001 | Inbar | 40/361 |
| 6,633,686 B1 | * | 10/2003 | Bakircioglu et al. | 382/294 |

FOREIGN PATENT DOCUMENTS

JP 11-202433 * 7/1999

* cited by examiner

*Primary Examiner*—Richard Hjerpe
*Assistant Examiner*—Abbas Abdulselam

(57) ABSTRACT

A digital system for evaluating foot and ankle radiographs having the advantage of providing accurate measurement information based on selected landmarks on the radiograph. The system includes a computing device, a coordinate generating digitizing device operatively connected to the computing device for generating coordinate data for the selected landmarks on the radiograph, and software for converting the coordinate data into descriptive measurement information. The present invention also includes a new method of analyzing foot and ankle radiographs that includes selecting a medical condition for evaluation, selecting a radiograph of the patient for the medical condition, determining landmarks to be located on the radiograph for evaluation of the medical condition, digitizing points in the landmark as coordinate data, and converting coordinate data into clinical measurement information. Another aspect of the invention includes the steps of defining and identifying a plurality of landmarks for a particular medical condition or evaluation.

35 Claims, 21 Drawing Sheets

28

Please Enter Patient Information ☒

*Patient Information*
MR# ▢
Last Name ▭
First Name ▭
Birthday ▢ / ▢ / ▢

Sex  ○ Male
     ○ Female

[ OK ]   [ Cancel ]

Date:
Hospital:
Physician:
Patient:
MR#
Right Foot
AP Standard
HAV/Bunion

| Measurement | Normal | Volume |
|---|---|---|
| Hallux Abductus Interphalangeus | 0-10 degrees | 2.9 |
| Hallas Abductus | 0-15 degrees | 28.5 |
| PASA | 0 to 8 degrees | 8.2 |
| DASA | 0 to 8 degrees | 0.1 |
| TASA | -5 to +5 degrees | 2.6 |
| Intermetatarsal Angle | 0-12 degrees | 10.8 |
| Relative Intermetatarsal Angle | 0-12 degrees | 10.7 |
| True Intermetatarsal Angle | 8 degrees | 13.0 |
| Metatarsus Adductus | <= 15 degrees | 17.2 |
| Engle's Angle | <18 degrees | 26.4 |
| Metatarsal Break Angle | 140 degrees | 146.9 |
| Joint Position | Congruous | Deviated |
| Tibial Sesamoid Position | TSP 1-3 | TSP=5 |
| Metatarsal Protrusion Distance | ± 2mm | 6.4mm |
| Metatarsal Deformation Angle | 0 to 8 degrees | 2.7 |
| Metatarsal Cuneiform Angle | 0-25 degrees | 32.2 |
| Metatarsus Varus Angle | <=25 degrees | 32.2 |
| 1st Met-Cuneiform/2nd Axis | N/A | 0.5 |
| Met Head Split Distance | N/A | 8.4mm |
| Met Base Split Distance | <2mm | 2.3mm |
| Forefoot Width | 7-9cm | 90.6mm |
| Tibial Sesamoid 2nd Met Distance | N/A | 27.8mm |

Fig. 8

HAV/BUNION KEY
*(AP Projection - Right)*

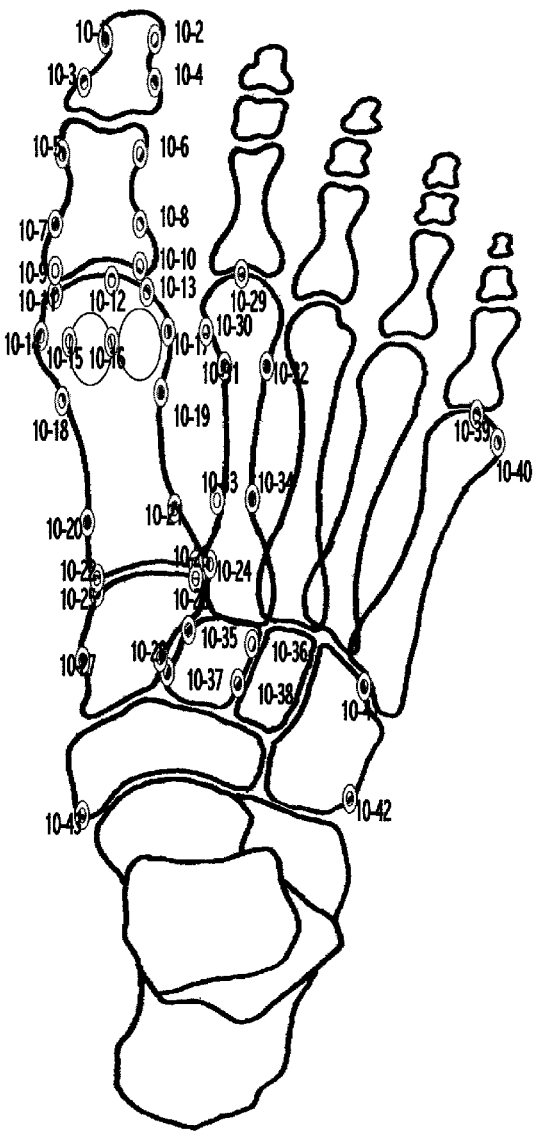

Fig. 10.

LANDMARKS:

1) Medial aspect of the distal diaphyseal – metaphyseal junction of the distal phalanx
2) Corresponding lateral aspect of the distal diaphyseal – metaphyseal junction of the distal phalanx
3) Medial aspect of the proximal diaphyseal – metaphyseal junction of the distal phalanx base
4) Corresponding lateral aspect of the proximal diaphyseal – metaphyseal junction of the distal phalanx base
5) Medial aspect of the distal diaphyseal – metaphyseal junction of the proximal phalanx
6) Corresponding lateral aspect of the distal diaphyseal – metaphyseal junction of the proximal phalanx
7) Medial aspect of the proximal diaphyseal – metaphyseal junction of the proximal phalanx base
8) Corresponding lateral aspect of the proximal diaphyseal – metaphyseal junction of the proximal phalanx base
9) Most medial aspect of the effective articular cartilage at the base of the proximal phalanx
10) Most lateral aspect of the effective articular cartilage at the base of the proximal phalanx
11) Most medial aspect of the effective articular cartilage of the 1$^{st}$ metatarsal head
12) Most distal aspect of the 1$^{st}$ metatarsal
13) Most lateral aspect of the effective articular cartilage of the 1$^{st}$ metatarsal head
14) Medial aspect of the 1$^{st}$ metatarsal head
15) Most medial aspect of the tibial sesamoid
16) Most lateral aspect of the tibial sesamoid
17) Corresponding lateral aspect of the 1$^{st}$ metatarsal head
18) Medial aspect of the distal diaphyseal – metaphyseal junction of the 1$^{st}$ metatarsal
19) Corresponding lateral aspect of the distal diaphyseal – metaphyseal junction of the 1$^{st}$ metatarsal
20) Medial aspect of the proximal diaphyseal – metaphyseal junction of the 1$^{st}$ metatarsal base
21) Corresponding lateral aspect of the proximal diaphyseal – metaphyseal junction of the 1$^{st}$ metatarsal base
22) Most proximal and medial aspect of the 1$^{st}$ metatarsal base
23) Most proximal and lateral aspect of the 1$^{st}$ metatarsal base
24) Most medial aspect of the 2$^{nd}$ metatarsal base adjacent to the most lateral aspect of the 1$^{st}$ metatarsal base
25) Most distal and medial aspect of the medial cuneiform
26) Most distal and lateral aspect of the medial cuneiform
27) Medial border of the 1$^{st}$ cuneiform approximately 1 sm distal to the cuneiform-navicular articulation
28) Corresponding lateral border of the 1$^{st}$ cuneiform
29) Most distal aspect of the 2$^{nd}$ metatarsal
30) Most medial aspect of the 2$^{nd}$ metatarsal head
31) Medial aspect of the distal diaphyseal – metaphyseal junction of the 2$^{nd}$ metatarsal
32) Corresponding lateral aspect of the distal diaphyseal – metaphyseal junction of the 2$^{nd}$ metatarsal
33) Medial aspect of the proximal diaphyseal – metaphyseal junction of the 2$^{nd}$ metatarsal base
34) Corresponding lateral aspect of the proximal diaphyseal – metaphyseal junction of the 2$^{nd}$ metatarsal base
35) Distal medial border of 2$^{rd}$ cuneiform
36) Corresponding lateral border of the 2$^{nd}$ cuneiform
37) Proximal medial border of the 2$^{nd}$ cuneiform
38) Corresponding proximal lateral border of the 2$^{nc}$ cuneiform
39) Most distal aspect of the 5$^{th}$ metatarsal
40) Most lateral aspect of the 5$^{th}$ metatarsal head
41) Most distal lateral aspect of cuboid-4$^{th}$ metatarsal articulation
42) Most proximal lateral aspect of the cuboid
43) Most proximal medial aspect of the talo-navicular articulation

HAV/BUNION
(AP Projection)

| MEASUREMENTS: | LANDMARKS: |
|---|---|
| Hallux Abductus Interphalangeal Angle | 10-1,2,3,4,5,6,7,8 |
| Hallux Abductus Angle | 10-5,6,7,8,18,19,20,21 |
| Proximal Articular Set Angle (PASA) | 10-11,13,18,19,20,21 |
| Distal Articular Set Angle (DASA) | 10-5,6,7,8,9,10 |
| Tangential Angle to the Second Axis (TASA) | 10-11,13,31,32,33,34 |
| Intermetatarsal Angle | 10-18,19,20,21,31,32,33,34 |
| Relative Intermetatarsal Angle | 10-14,17,20,21,31,32,33,34 |
| "True" Intermetatarsal Angle | 10-18,19,20,21,31,32,33,34,25,41,42,43 |
| Metatarsus Adductus Angle | 10-31,32,33,34,25,41,42,43 |
| Engle's Angle | 10-31,32,33,34,35,36,37,38 |
| Metatarsal Break Angle | 10-12,29,39 |
| 1st MPJ Position | 10-9,10,11,13 |
| IM Cortical Angle | 10-21,23,24,33 |
| Tibial Sesamoid Position (TSP) | 10-15,16,18,19,20,21 |
| Relative TSP | 10-14,15,16,17,20,21 |
| Metatarsal Protrusion Distance | 10-12,18,19,20,21,29,31,32,33,34 |
| 1st Metatarsal Deformation Angle | 10-18,19,20,21,22,23 |
| 1st Met-Cuneiform Angle | 10-18,19,20,21,25,26,27,28 |
| Metatarsal Varus Angle 1st | 10-18,19,20,21,25,26,27,28 |
| Met-Cuneiform / 2nd Axis | 10-25,26,31,32,33,34 |
| Metatarsal Head Split Distance | 10-17,30 |
| Metatarsal Base Split Distance | 10-23,24 |
| Forefoot Width | 10-14-40 |
| Tibial Sesamoid-2nd Metatarsal Distance | 10-7,14,15,16,17 |

*Fig. 11*

TAILOR'S BUNION KEY
*(AP Projection - Right)*

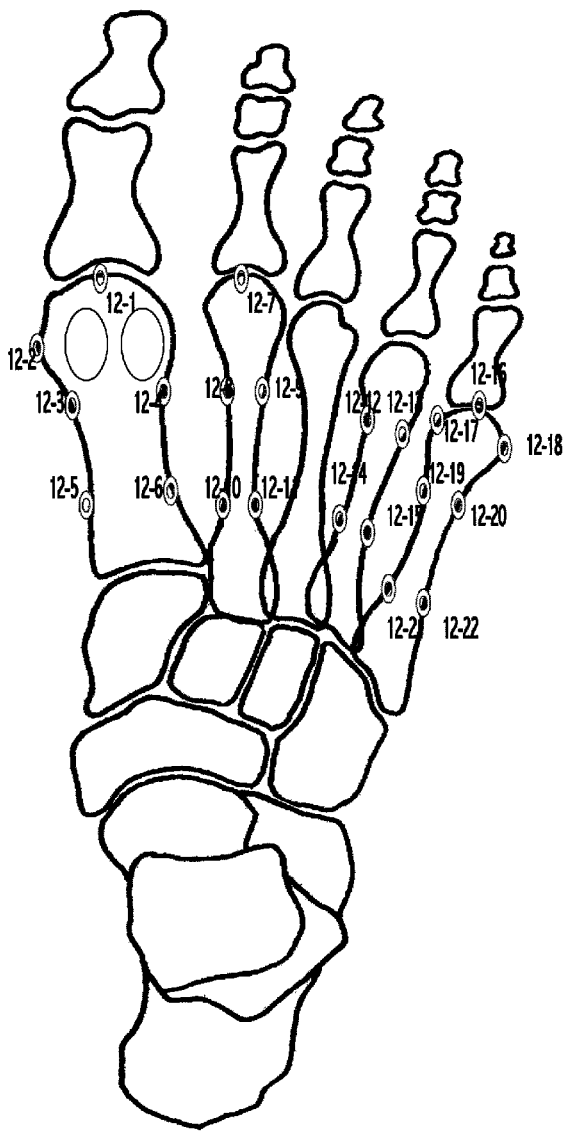

LANDMARKS

1) Most distal aspect of the 1st metatarsal
2) Most medial aspect of the 1 metatarsal head
3) Medial aspect of the distal diaphyseal-metaphyseal junction of the 1st metatarsal
4) Corresponding lateral aspect of the distal diaphyseal-metaphyseal junction of the 1st metatarsal
5) Medial aspect of the proximal diaphyseal-metaphyseal junction of the 1st metatarsal
6) Corresponding lateral aspect of the proximal diaphyseal-metaphyseal junction of the 1st metatarsal
7) Most distal aspect of the 2nd metatarsal
8) Medial aspect of the distal diaphyseal-metaphyseal junction of the 2nd metatarsal
9) Corresponding lateral aspect of the distal diaphyseal-metaphyseal junction of the 2nd metatarsal
10) Medial aspect of the proximal diaphyseal-metaphyseal junction of the 2nd metatarsal
11) Corresponding lateral aspect of the proximal diaphyseal-metaphyseal junction of the 2nd metatarsal
12) Medial aspect of the distal diaphyseal-metaphyseal junction of the 4th metatarsal
13) Corresponding lateral aspect of the distal diaphyseal-metaphyseal junction of the 4th metatarsal
14) Medial aspect of the proximal diaphyseal-metaphyseal junction of the 4th metatarsal
15) Corresponding lateral aspect of the proximal diaphyseal-metaphyseal junction of the 4th metatarsal
16) Most distal aspect of the 5th metatarsal
17) Medial aspect of 5th metatarsal head
18) Lateral aspect of 5th metatarsal head
19) Medial aspect of the distal diaphyseal-metaphyseal junction of the 5th metatarsal
20) Corresponding lateral aspect of the distal diaphyseal-metaphyseal junction of the 5th metatarsal
21) Medial aspect of the proximal diaphyseal-metaphyseal junction of the 5th metatarsal
22) Corresponding lateral aspect of the proximal diaphyseal-metaphyseal junction of the 5th metatarsal

*Fig. 12*

| MEASUREMENTS: | LANDMARKS |
|---|---|
| 4/5 Intermetatarsal Angle (traditional) | 12-12,13,14,15,19,20,21,22 |
| 4/5 Intermetatarsal Angle (Fallat & Buckholz) | 12-12,13,14,15,19,21 |
| 2/5 Intermetatarsal Angle | 12-8,9,10,11,19,20,21,22 |
| $1^{st}$ Intermetatarsal Angle | 12-3,4,5,6,8,9,10,11 |
| Forefoot Width | 12-2,18 |
| $5^{th}$ Metatarsal Lateral Deviation Angle | 12-17,18,19,20,21 |
| Metatarsal Break Angle | 12-1,7,16 |

TAILOR'S BUNION
(AP Projection)

STANDARD LATERAL KEY
*(Intended for HAV, Tailor's Bunion & Haglund's Evaluations)*

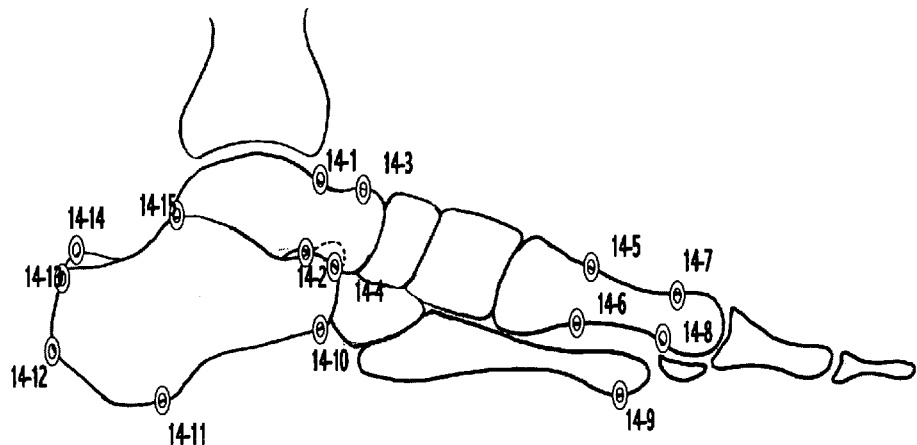

LANDMARKS:

1) Dorsal proximal aspect of the neck of the talus
2) Corresponding plantar proximal aspect of the neck of the talus
3) Dorsal distal aspect of the head of the talus
4) Corresponding plantar distal aspect of the head of the talus
5) Dorsal aspect of $1^{st}$ metatarsal proximal metaphyseal – diaphyseal junction
6) Corresponding plantar aspect of $1^{st}$ metatarsal proximal metaphyseal -diaphyseal junction
7) Dorsal aspect of $1^{st}$ metatarsal distal metaphyseal – diaphyseal junction
8) Corresponding plantar aspect of $1^{st}$ metatarsal metaphyseal – diaphyseal junction
9) Most plantar aspect of the $5^{th}$ metatarsal head
10) Most plantar distal aspect of the calcaneus at the calcaneal-cuboid joint
11) Most plantar aspect of the calcaneal tuberosity
12) Most posterior aspect of the calcaneus at the middle 1/3 of its posterior border
13) Most superior aspect of the posterior border of the calcaneus
14) Most superior aspect of posterior-superior bursal projection
15) Most posterior and superior point of the posterior articular surface of the calcaneus

*Fig. 14*

STANDARD LATERAL
(For HAV, Tailor's & Haglund's)

| MEASUREMENTS: | LANDMARKS: |
|---|---|
| Calcaneal Inclination Angle | 14-9,10,11 |
| Talar Declination Angle | 14-1,2,3,4,9,11 |
| Lateral Talocalcaneal Angle | 14-1,2,3,4,10,11 |
| First Metatarsal Declination Angle | 14-5,6,7,8,9,11 |
| Lateral Talo-1st Metatarsal Angle | 14-1,2,3,4,5,6,7,8 |
| Fowler-Philip Angle | 14-10,11,12,13 |
| Total Angle | 14-9,11,12,13 |
| Parallel Pitch Lines | 14-10,11,14,15 |

CALCANEAL TRAUMA KEY
*(Lateral Projection - Right)*

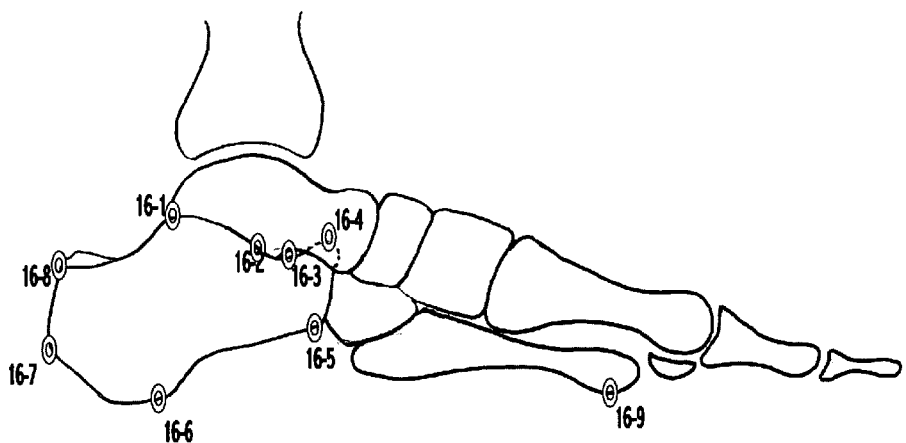

LANDMARKS:

1) Most posterior and superior point of the posterior articular surface of the calcaneus
2) Most anterior and inferior point of the posterior articular surface of the calcaneus
3) Most posterior and inferior point of the middle articular surface of the calcaneus
4) Most superior and anterior point of the anterior articular surface of the calcaneus
5) Most plantar distal aspect of the calcaneus at the calcaneal-cuboid joint
6) Most plantar aspect of the calcaneal tuberosity
7) Most posterior aspect of the calcaneus at the middle 1/3 of its posterior border
8) Most superior aspect of the posterior border of the calcaneus
9) Most plantar aspect of the $5^{th}$ metatarsal head

*Fig. 16*

CALCANEAL TRAUMA
(Lateral Projection)

| MEASUREMENTS: | LANDMARKS: |
|---|---|
| Boehler's Angle | 16-1,4,8 |
| Gissane's Crucial Angle | 16-1,2,3,4 |
| Posterior Facet Angle of Inclination | 16-1,2,6,9 |
| Calcaneal Inclination Angle | 16-5,6,9 |
| Calcaneal Compression Angle | 16-1,4,5,6 |

BIOMECHANICAL EVALUATION KEY
*(AP Projection - Right)*

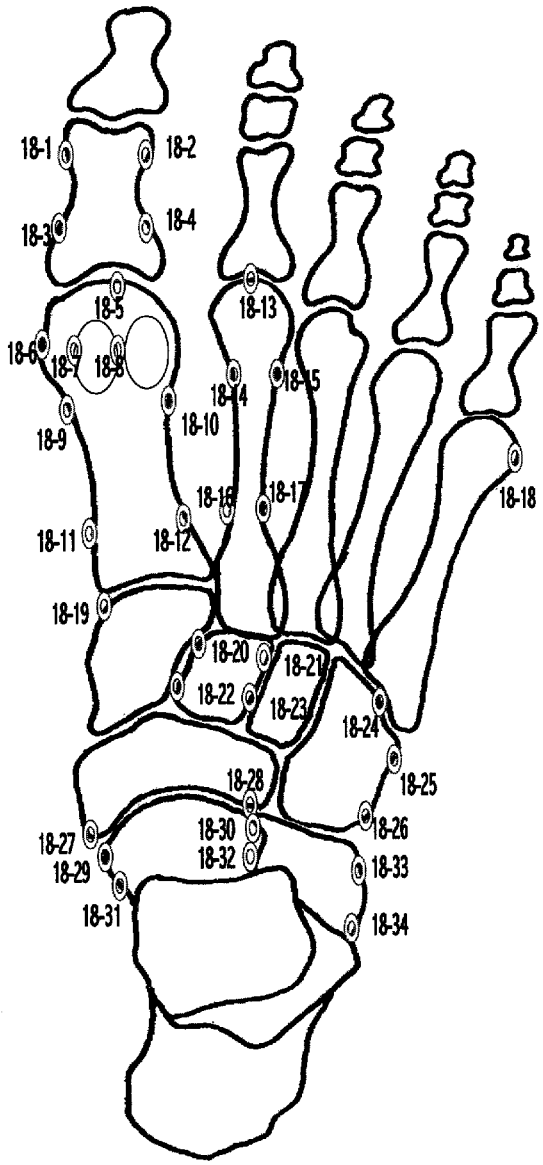

LANDMARKS:

1) Medial aspect of the distal diaphyseal – metaphyseal junction of the proximal phalanx
2) Corresponding lateral aspect of the distal diaphyseal – metaphyseal junction of the proximal phalanx
3) Medial aspect of the proximal diaphyseal – metaphyseal junction of the proximal phalanx base
4) Corresponding lateral aspect of the proximal diaphyseal – metaphyseal junction of the proximal phalanx base
5) Most distal aspect of the $1^{st}$ metatarsal
6) Medial aspect of the $1^{st}$ metatarsal head
7) Most medial aspect of the tibial sesamoid
8) Most lateral aspect of the tibial sesamoid
9) Medial aspect of the distal diaphyseal – metaphyseal junction of the $1^{st}$ metatarsal
10) Corresponding lateral aspect of the distal diaphyseal – metaphyseal junction of the $1^{st}$ metatarsal
11) Medial aspect of the proximal diaphyseal – metaphyseal junction of the $1^{st}$ metatarsal base
12) Corresponding lateral aspect of the proximal diaphyseal – metaphyseal junction of the $1^{st}$ metatarsal base
13) Most distal aspect of the $2^{nd}$ metatarsal
14) Medial aspect of the distal diaphyseal – metaphyseal junction of the $2^{nd}$ metatarsal
15) Corresponding lateral aspect of the distal diaphyseal – metaphyseal junction of the $2^{nd}$ metatarsal
16) Medial aspect of the proximal diaphyseal – metaphyseal junction of the $2^{nd}$ metatarsal base
17) Corresponding lateral aspect of the proximal diaphyseal – metaphyseal junction of the $2^{nd}$ metatarsal base
18) Lateral aspect of the $5^{th}$ metatarsal head
19) Most distal and medial aspect of the medial cuneiform
20) Distal medial border of $2^{nd}$ cuneiform
21) Corresponding lateral border of the $2^{nd}$ cuneiform
22) Proximal medial border of the $2^{nd}$ cuneiform
23) Corresponding proximal lateral border of the $2^{nd}$ cuneiform
24) Most distal lateral aspect of cuboid-$4^{th}$ metatarsal articulation
25) Most distal aspect of the lateral border of the cuboid
26) Most proximal and lateral aspect of the cuboid
27) Most proximal medial aspect of the navicular
28) Most proximal and lateral aspect of the navicular
29) Medial aspect of the head of the talus
30) Corresponding lateral aspect of the head of the talus
31) Medial aspect of the neck of the talus
32) Corresponding lateral aspect of the neck of the talus
33) Distal lateral aspect of the lateral calcaneal border
34) Corresponeding point 1-2 cm proximal to point # 32 at the lateral calcaneal border.

*Fig. 18*

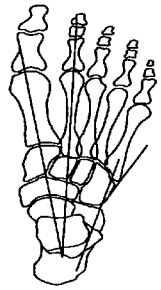

BIOMECHANICAL
(AP Projection)

| MEASUREMENTS: | LANDMARKS: |
|---|---|
| Hallux Abductus Angle | 18-1,2,3,4,9,10,11,12 |
| Intermetatarsal Angle | 18-9,10,11,12,14,15,16,17 |
| "True" Intermetatarsal Angle | 18-9,10,11,12,14,15,16,17,19,24,26,27 |
| Metatarsus Adductus Angle | 18-14,15,16,17,19,24,26,27 |
| Engle's Angle | 18-14,15,16,17,20,21,22,23 |
| Forefoot Width | 18-6,18 |
| Tibial Sesamoid Position | 18-7,8,9,10,11,12 |
| Tibial Sesamoid $2^{nd}$ Metatarsal Distance | 18-7,14,15,16,17 |
| Metatarsal Protrusion Distance | 18-5,9,10,11,12,13,114,15,16,17 |
| Cuboid Abduction Angle | 18-25,26,33,34 |
| Forefoot Adductus Angle | 18-14,15,16,17,33,34 |
| Percent of Talo-Navicular Articulation | 18-27,29,30 |
| Talocalcaneal Angle (Kite's Angle) | 18-29,30,31,32,33,34 |
| Lesser Tarsus Abductus Angle | 18-19,24,26,27,33,34 |
| $1^{st}$ Metatarsal-Calcaneal Angle | 18-9,10,11,12,33,34 |

*Fig. 19*

BIOMECHANICAL - LAT EVALUATION KEY
*(Lateral Projection - Right)*

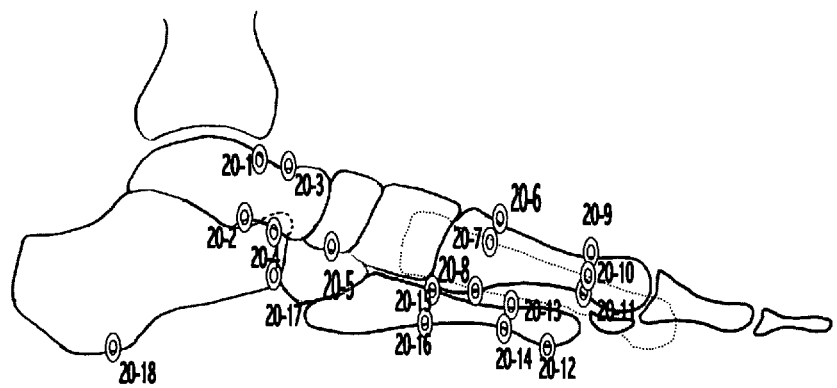

LANDMARKS:

1) Dorsal proximal aspect of the neck of the talus
2) Corresponding plantar proximal aspect of the neck of the talus
3) Dorsal distal aspect of the head of the talus
4) Corresponding plantar distal aspect of the head of the talus
5) Most plantar aspect of the navicular
6) Dorsal aspect of the $1^{st}$ metatarsal proximal metaphyseal – diaphyseal junction approximately 1.5 cm distal to its articular base
7) A point on the proximal dorsal aspect of the $2^{nd}$ metatarsal corresponding to point #6 on the $1^{st}$ metatarsal.
8) Plantar aspect of $1^{st}$ metatarsal proximal metaphyseal -diaphyseal junction corresponding to point #6
9) Dorsal aspect of $1^{st}$ metatarsal distal metaphyseal – diaphyseal junction
10) Dorsal aspect of the $2^{nd}$ metatarsal shaft corresponding to point #9 on the $1^{st}$ metatarsal
11) Plantar aspect of $1^{st}$ metatarsal distal metaphyseal – diaphyseal junction corresponding to point #9
12) Most plantar aspect of the $5^{th}$ metatarsal head
13) Dorsal aspect of the $5^{th}$ metatarsal distal metaphyseal – diaphyseal junction
14) Corresponding plantar aspect of the $5^{th}$ metatarsal distal metaphyseal – diaphyseal junction
15) Dorsal aspect of the $5^{th}$ metatarsal proximal metaphyseal – diaphyseal junction
16) Plantar aspect of the $5^{th}$ metatarsal proximal metaphyseal – diaphyseal junction
17) Most plantar distal aspect of the calcaneus at the calcaneal-cuboid joint
18) Most plantar aspect of the calcaneal tuberosity

*Fig. 20*

BIOMECHANICAL
(Lateral Projection)

| MEASUREMENTS: | LANDMARKS: |
|---|---|
| Calcaneal Inclination Angle | 20-12,17,18 |
| Talar Declination Angle | 20-1,2,3,4,12,18 |
| Lateral Talocalcaneal Angle | 20-1,2,3,4,17,18 |
| 1st Metatarsal Declination Angle | 20-6,8,9,11,12,18 |
| Seiberg Index | 20-6,7,9,10 |
| Lateral Talo-1st Metatarsal Angle | 20-1,2,3,4,6,8,9,11 |
| 5th Metatarsal Declination Angle | 20-12,13,14,15,16,18 |
| Height of the Navicular | 20-5,12,18 |

DIGITAL RADIOGRAPH ANALYZER AND METHODS

BACKGROUND OF THE INVENTION

1. Field of the Invention

The present invention relates to medical equipment and methods for evaluating radiographs. More particularly, though not exclusively, the present invention relates to a digital radiograph analyzer, software, and methods for evaluating foot and ankle radiographs.

2. Problems in the Art

Physicians and other care providers have long recognized the value of measuring and comparing osseous relationships. Having the benefit of various angles and distances on a patient's radiograph can be helpful in evaluating different medical conditions. Podiatric physicians have utilized this information concerning the foot and ankle in preoperative and postoperative evaluation, following traumatic injury and in biomechanical assessments.

Although prior art equipment and methods for quantifying osseous relationships have enjoyed some success, they suffer from several inherent problems. The first problem concerns the accuracy of the measurements. Manual radiograph measurement is often used in quantifying the osseous relationships in the foot and ankle. In this prior art method, measurements are determined by selecting landmarks on the radiograph. Lines between selected landmarks or points are drawn with a wax pen and the relative angles measured using a tractograph, goniometer or protractor. Unfortunately, this manual method is often unreliable and inaccurate due to landmark variability, line drawing variability and lack of standardization of the measuring device. And yet physicians rely upon these measurements in making decisions about treatment. Not only does the quality of care suffer, but physicians are at a greater risk of being subjected to malpractice claims. Thus, there is a need in the art for a more accurate and reliable means and method of measuring the osseous relationships in foot and ankle radiographs.

Important to the accuracy of the foot and ankle measurements is the selection of proper landmarks on the radiograph. For instance, to accurately measure the angle between lines on a foot radiograph, the clinician must select landmarks on the radiograph that accurately define the two lines. Much has been written regarding the use of landmarks in quantifying the osseous relationships in foot and ankle radiographs. However, there are no standard sets of landmarks for evaluating foot and ankle conditions. Thus, there is also a need in the art for a defined set of landmarks from which clinically useful measurement information could be derived concerning a particular condition.

Prior art methods of radiograph evaluation tend to be tedious and time-consuming. It is common for clinicians to spend ten to fifteen minutes in measuring a radiograph for a particular foot and ankle condition. This becomes a labor-intensive process for clinicians and office staff, diverting resources away from other care giving activities. Thus, there is also a need in the art for a more efficient means and method of evaluating foot and ankle radiographs.

Prior art methods of radiograph measurement and evaluation also do not lend themselves easily to private practice and outcomes research. Patient information regarding age, sex, preoperative measurements, procedure and postoperative measurements is not generally maintained in a digital format in a central location that can be accessed by means of a computer. It would be helpful for physicians and researchers to have the benefit of historical patient data for practice management applications and outcomes research. A need therefore also exists in the art for an improved means and method of evaluating foot and ankle radiographs wherein the clinical measurements are captured and can be easily accessed for practice management and outcomes research studies.

Features of the Invention

A general feature of the present invention is the provision of an improved radiograph analyzer, software and methods, which overcome the deficiencies found in the prior art.

A further feature of the present invention is the provision of a radiograph analyzer for podiatric applications that provides useful clinical measurement information that is reliable and accurate.

A still further feature of the present invention is the provision of a radiograph analyzer that is efficient in operation, reducing the time required to quantitatively evaluate foot and ankle radiographs.

A still further feature of the present invention is the provision of computer software to facilitate the conversion of landmark coordinates into useful clinical measurement information.

Another feature of the present invention is the provision of a radiograph analyzer having the ability to store patient data for later use in practice management applications and outcomes research.

Another feature of the present invention is a new method for evaluating ankle and foot radiographs using a coordinate generating digitizing device.

Yet another feature of the present invention is the provision of a new method of evaluating foot and ankle radiographs that is fast, efficient and accurate.

These as well as other features and advantages of the present invention will become apparent from the following specification and claims.

SUMMARY OF THE INVENTION

The present invention includes a digital system for evaluating foot and ankle radiographs. The digital system includes a computing device, a coordinate generating digitizing device connected to the computing device, and computer software for converting landmark coordinate data from the radiograph into clinically descriptive measurement information. Using such a system, a clinician or other healthcare provider can quickly "digitize" the appropriate landmarks on the radiograph for a particular podiatric evaluation. Once the landmarks have been digitized, the software computes angles and distances, quantifying the osseous relationships in the foot and ankle.

Another aspect of the invention is software particularly adapted for analyzing radiographs of the foot and ankle for various medical conditions. The software determines landmarks in the radiograph to be located, reads the coordinate data for the landmarks, and converts the coordinate data into clinically descriptive measurement information.

Yet another aspect of the present invention includes a method of analyzing foot and ankle radiographs. This method generally includes the steps of selecting a medical condition for evaluation, selecting a radiograph of the patient corresponding to the medical condition, determining landmarks to be located on the radiographs for evaluation of the medical condition, digitizing points for the landmarks as coordinate data, and converting the coordinate data into clinical measurement information. In a preferred form, this information may be displayed along with normal values for comparison purposes.

In yet another aspect of the invention, a method of analyzing foot and ankle radiographs includes the steps of defining and identifying a plurality of landmarks relevant to a particular evaluation. As explained previously, the proper definition and identification of landmarks is important to ensure accurate measurements.

BRIEF DESCRIPTION OF THE DRAWINGS

FIG. 3 is a new patient information window of the software application of the present invention.

FIG. 7 is a digitizing window of the software application of the present invention.

FIG. 8 is an example of an output screen in table format.

FIG. 10 is a HAV/Bunion evaluation landmark key.

FIG. 11 is a diagram illustrating HAV/Bunion measurements.

FIG. 12 is a Tailor's Bunion evaluation landmark key.

FIG. 14 is a Standard Lateral evaluation landmark key.

FIG. 16 is a Calcaneal Trauma evaluation landmark key.

FIG. 18 is a Biomechanical (AP Projection) evaluation landmark key.

FIG. 19 is a diagram illustrating Biomechanical (AP Projection) measurements.

FIG. 20 is a Biomechanical (Lateral Projection) evaluation landmark key.

DETAILED DESCRIPTION OF THE PREFERRED EMBODIMENT

The present invention will be described as it applies to a preferred embodiment. It is not intended that the present invention be limited to the described embodiment. It is intended that the invention cover all modifications and alternatives which may be included within the spirit and broad scope of the invention.

Figure 1:
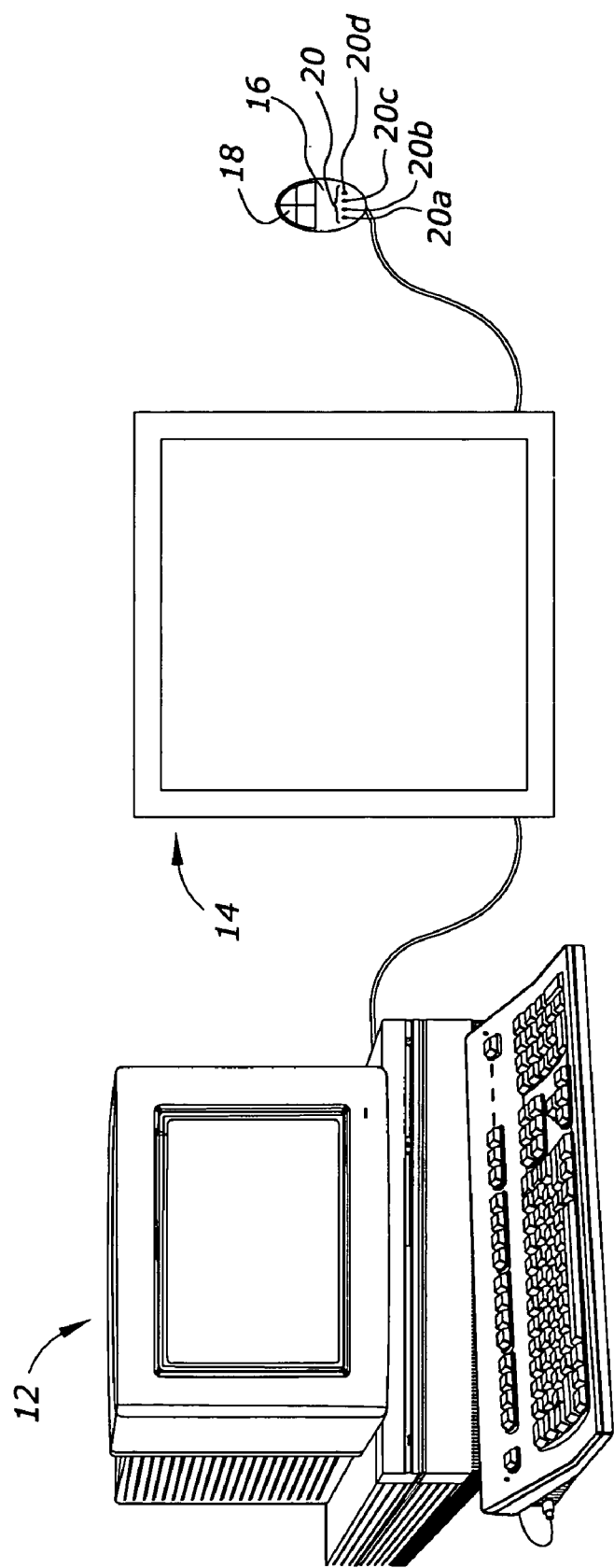
FIG. 1 is a diagram of the technical architecture of the digital radiograph analyzer of the present invention.

Now, referring to the drawings, FIG. 1 illustrates the technical architecture of the present invention. The digital radiograph analyzer 10 includes a computer workstation 12 and a coordinate generating digitizing device (or digitizer) 14. A variety of different digitizing devices 14 suitable for use in the present invention are commercially available. The AccuGrid backlighted digitizers, Models A30BL and A43BL, by Numonics Corporation, are preferred. The digitizing device 14 includes a cursor 16 with a crosshair 18 and a plurality of different function buttons 20. As is explained in more detail below, the clinician uses the cursor 16 to select certain landmarks on a radiograph to be digitized and entered into the system for analysis by the software application.

The user interface preferred for use by the workstation is a graphical user interface (GUI), running for example on a Microsoft (MS) Windows 95/98 or MS Windows NT platform. The software application is a 32-bit application designed to run on MS Windows 95/98 and NT platforms, which may be developed using C++ or other object-oriented language. The purpose of the software application is analyze coordinate data from the digitizing device 14 to provide clinically useful measurement information for purposes of evaluation by a physician or other care giver.

Those skilled in the art will appreciate that various other technical configurations can be utilized. By way of example only, the workstation 12 could be connected to a local area network in a client-server configuration. All patient data could be then stored in a central server location which would be accessible throughout the network. The present invention could also be used in Intranet and Internet applications. For example, the software application could reside on an application server accessible via the Internet.

With the technical architecture described above, the logic or methods necessary to give the software application flow and functionality becomes readily apparent to those skilled in the art from a review of the principal windows or screen displays.

Figure 2:
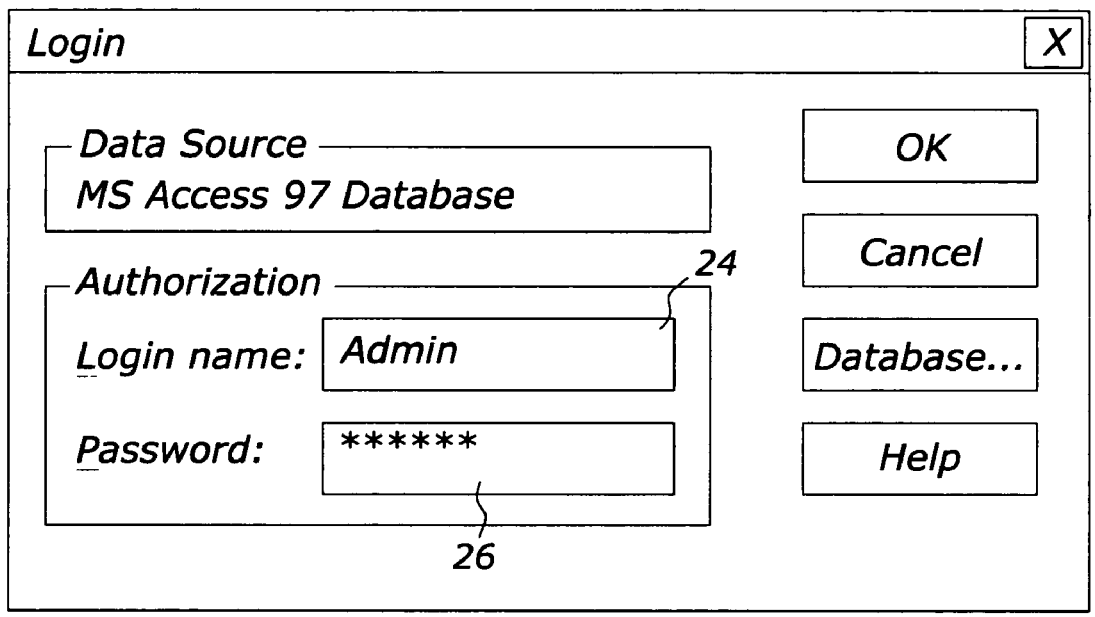
FIG. 2 is a login window of the software application of the present invention.

FIG. 2 shows a login screen 22 of the software application. Due to the sensitive nature of patient records, the patient information and evaluation results are preferably password protected. The clinician or other user of the system must provide a login name and patient database password in the login field 24 and the password field 26, respectively.

Upon entering the system, the clinician has the option of either creating a new patient record or accessing an existing one. FIG. 3 is a new patient information window 28, illustrating the types of information required to create a new patient record. The patient information includes name, birth date, sex and MR number. Of course, this window could easily be customized by those skilled in the art if different or additional patient information is preferred.

Figure 4:
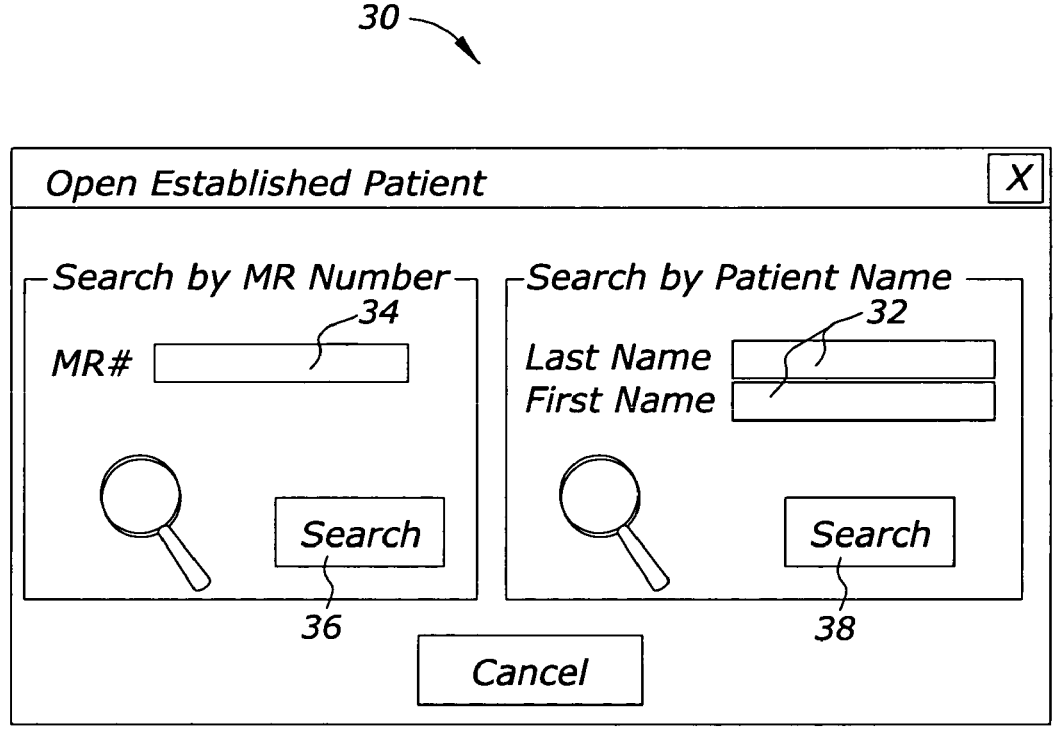
FIG. 4 is a patient search window of the software application of the present invention.

If patient information has previously been entered, the clinician can use the patient search window 30 (shown in FIG. 4) to search for the patient's record. The clinician can search by either name or MR number, using the name fields 32 or MR number field 34. A single click or selection of the corresponding search push buttons 36 and 38 initiates the search of patient records.

Figure 5:
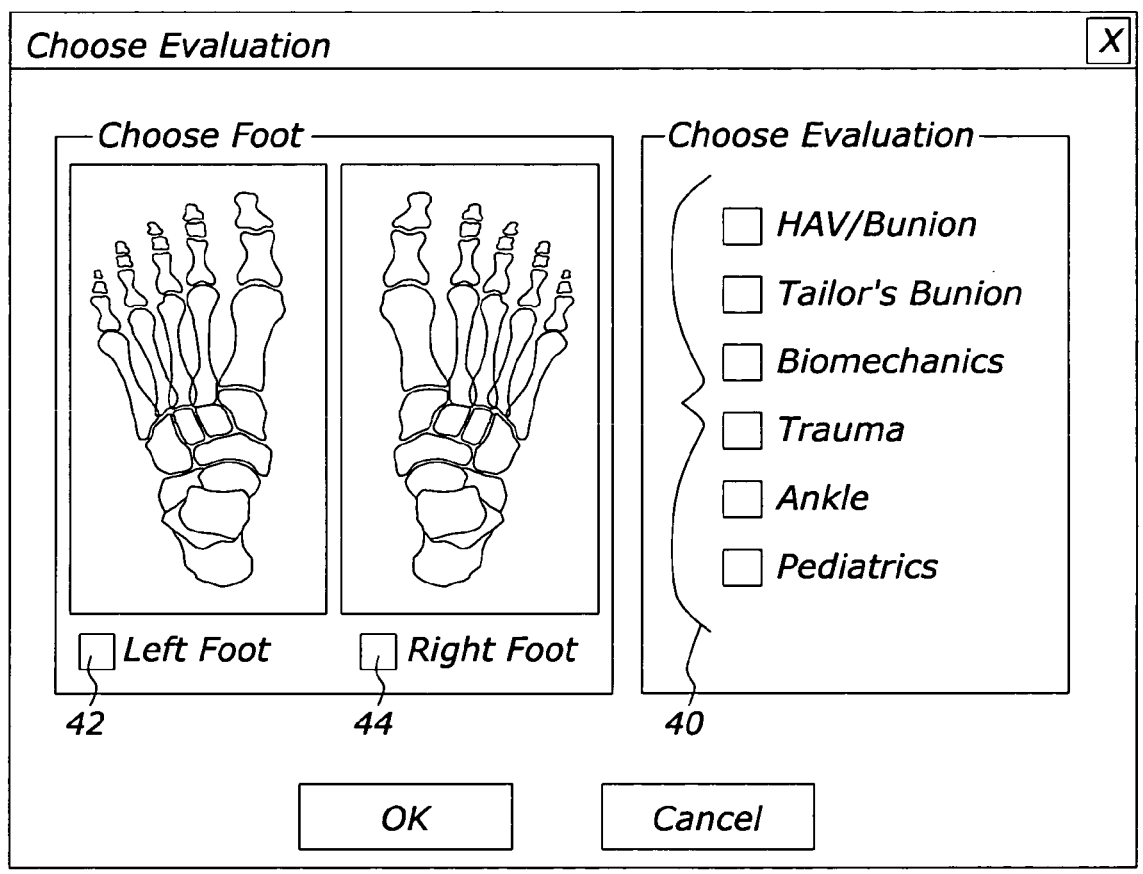
FIG. 5 is an evaluation selection window of the software application of the present invention.

Once the clinician has entered new patient information or selected an existing patient record, the clinician chooses the appropriate evaluation. As illustrated in the evaluation selection window 38 in FIG. 5, a plurality of check boxes 40 are provided for different evaluations/medical conditions. The clinician can also choose to evaluate the patient's right or left foot by selecting of the appropriate check boxes 42 and 44.

Figure 6:
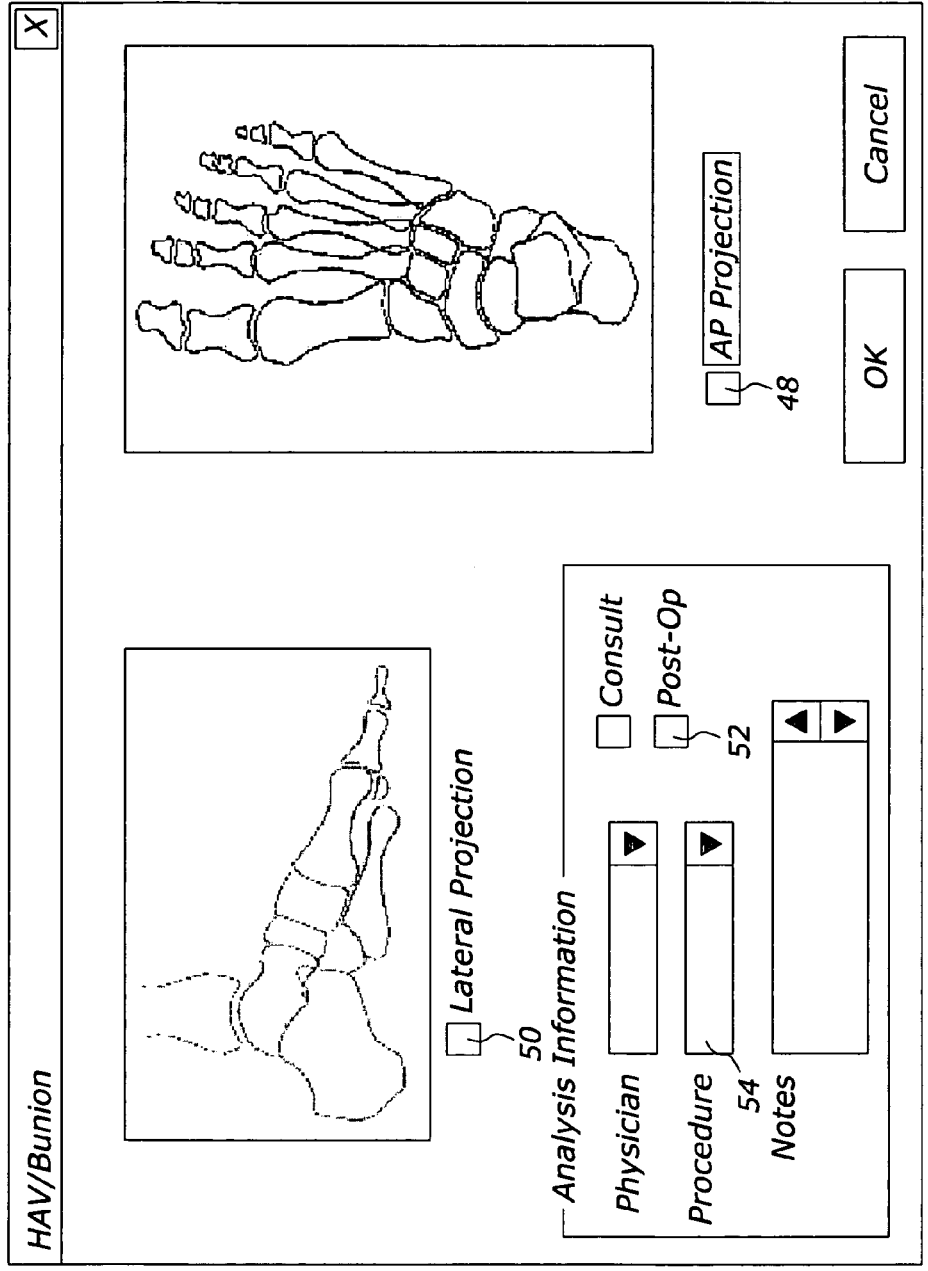
FIG. 6 is a radiograph selection window of the software application of the present invention.

After choosing the desired evaluation, the clinician chooses a particular radiograph to digitize. FIG. 6 illustrates the radiograph selection window 46 for an HAV/Bunion evaluation. For this particular evaluation, the clinician can choose either an AP projection or a lateral projection to digitize by selection of the check boxes 48 and 50. Note also that the clinician can enter the name of the physician evaluating the patient and whether it is a first time evaluation (consult) or a post-op evaluation. When the post-op check box 52 is marked, a list of procedure names can be scrolled through in the procedure drop-down box 54 and the procedure that was performed can be selected. This information can be useful to complete evaluation data, facilitate research, and perform practice management tasks.

Figure 7:
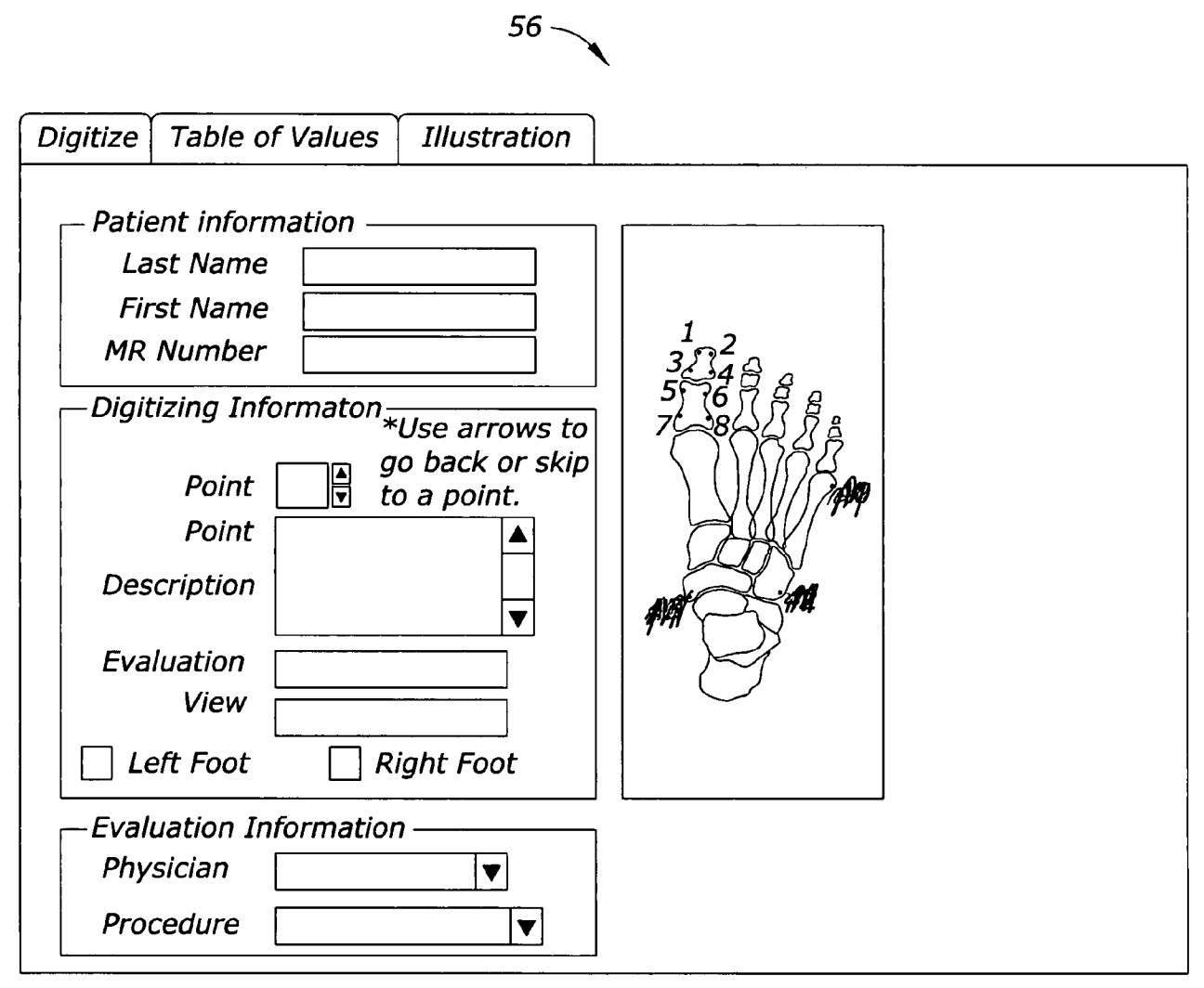

After selecting the radiograph evaluation information, the clinician is next presented with the digitizing window 56 as shown in FIG. 7. At this point it is important that the clinician have the digitizing device 14 powered on and the appropriate radiograph secured to the surface of the digitizer. Using the cursor 16 of the digitizing device 14, the clinician now proceeds to digitize the various landmark positions on the radiograph required for the evaluation. The clinician should have the benefit of an evaluation key that indicates what specific landmarks are required for a particular evaluation. Specific landmark keys and their intended use are described in more detail later in the specification.

Several of the function buttons 20 on the cursor 16 are programmed to facilitate the digitizing process. For example, function button 20a is used to digitize a landmark or point. Function button 20b is selected to return to a previous point. Function button 20c is used to skip to a particular point, and function button 20d is used to skip the remaining points in the evaluation. The digitizing task is accomplished by centering the crosshairs 18 of the cursor 16 directly over the landmark on the radiograph to be digitized and pressing function button 20a on the cursor. It is important to input the landmarks correctly, as this is the information used to complete the measurement computations. The preferred digitizer 14 has resolution of up to ⅟₁₀₀ of a millimeter and will record the landmark exactly as it is entered. A previous point may be redigitized by pressing the function button 20b on the cursor to backup one point and then digitize again by pressing function button 20a. As shown in the graphical illustration of the radiograph in FIG. 7, the landmarks digitized are displayed with a reference numeral to identify particular landmarks.

If the clinician does not wish to have the benefit of all the available measurements for a given evaluation, the software application is designed to allow the clinician to enter only the landmarks necessary for the measurements desired. The clinician would reference the directory of measurements to determine the landmarks used for the designed measurements and use the cursor function buttons 20 to skip landmarks as appropriate.

Once the landmarks are digitized, the software application uses the coordinate data to compute or quantify the osseous relationships on the radiograph. This may include angles, distances and other quantitative information. This clinically useful measurement information can be displayed on an output monitor or in hard copy format. FIG. 8 illustrates the measurement information for an HAV/Bunion evaluation in a table format 58. Note that the type of measurement is shown in column 60, the normal values shown in column 62, and the measured values are shown in column 64. Providing normal values along with the measured values provides a useful comparison that the physician or other care giver can use in quickly evaluating the results and making treatment decisions.

Figure 9:
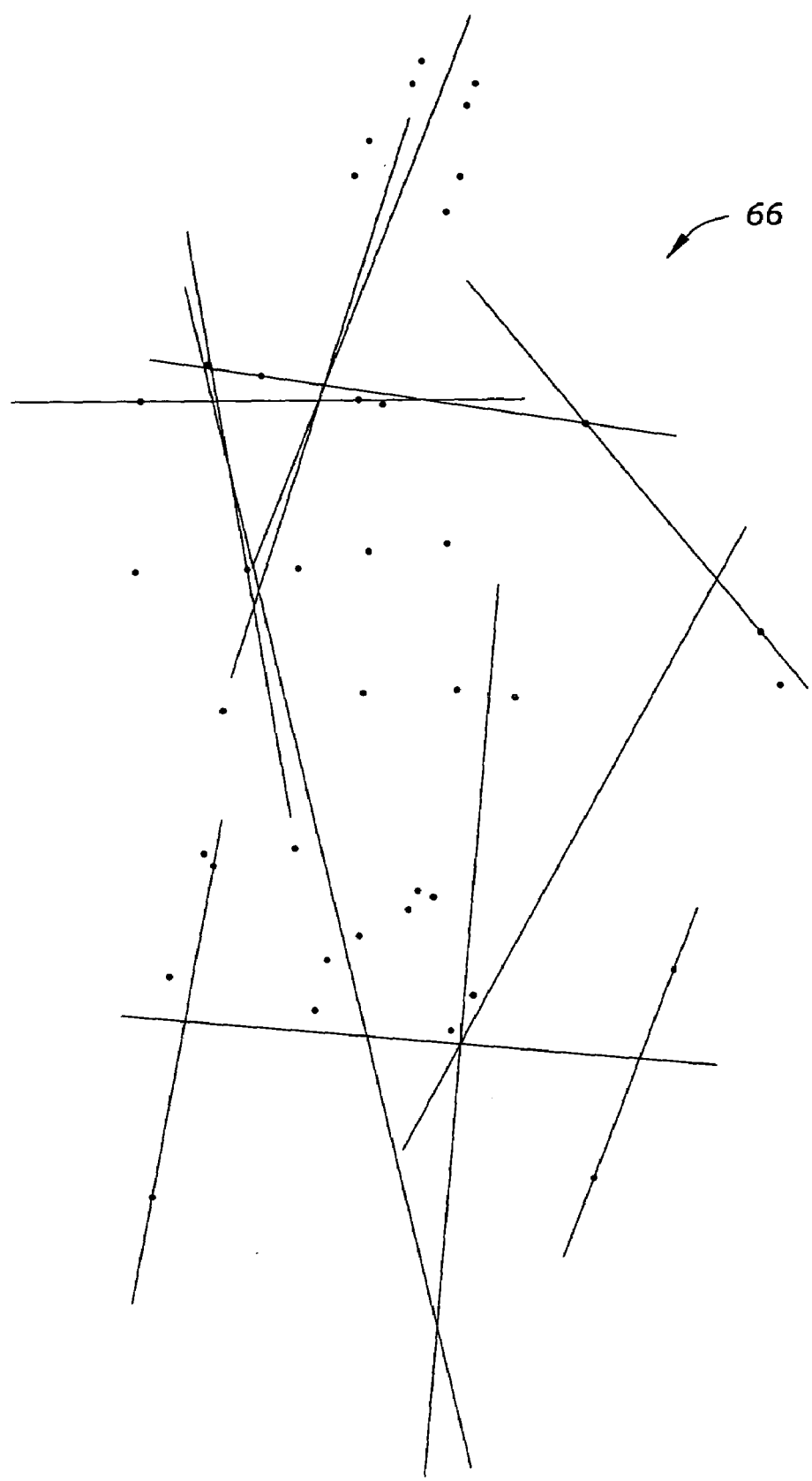
FIG. 9 is an example of an output screen in graphical format.

FIG. 9 shows the graphical representation 66 of the different landmarks that were digitized with lines drawn to illustrate the various angles measured.

Note that the preferred embodiment was illustrated with the medical condition or evaluation as HAV/Bunion. In digitizing the various points for the HAV/Bunion evaluation, the clinician would consult a landmark key as shown in FIG. 10. Landmarks 10-1 through 10-43 are defined in FIG. 10 for purposes of completing a full HAV/Bunion evaluation. The measurements associated with the HAV/Bunion evaluation are shown in FIG. 11, along with the specific landmarks that must be digitized in order to compute a particular measurement. Applications for the HAV/Bunion measurements are described below. The normal values provided may, in some instances, be the subject of some disagreement in the field.

The Hallux Abductus Interphalangeal Angle (HAIA) illustrates the alignment of the distal and proximal phalanx at the interphalangeal joint of the hallux. When this angle is abnormally increased, the distal portion of the hallux may impinge on the second digit and thus create additional problems. Correction of this deformity is typically addressed at the head of the proximal phalanx. Lack of properly identifying an abnormal HAIA can lead to over correction of the hallux abductus angle with an aggressive capsulorrhaphy. Normal values for this angle range between 0–10°.

The Hallux Abductus Angle (HAA) is formed by the bisections of the proximal phalanx of the hallux and the $1^{st}$ metatarsal. The abductus deformity illustrated by this angle is of primary importance in a HAV condition. This angulation may be due to positional, structural or a combination of abnormalities. Normal values for this angle range between 0–15°.

The Proximal Articular Set Angle (PASA) is derived from a line representing the effective articular surface of the $1^{st}$ metatarsal head and a line perpendicular to the bisection of the $1^{st}$ metatarsal. Due to bony adaptation, PASA may be deviated laterally and increased in HAV deformities. Certain procedures at the head of $1^{st}$ metatarsal may be utilized to correct this malalignment. Normal values for this angle range between 0–8°.

The Distal Articular Set Angle (DASA) is derived from the line formed by the boundaries of the effective articular cartilage at the base of the proximal phalanx and a perpendicular to the bisection of the proximal phalanx. Correction of the bony adaptation in this abnormality typically occurs via a proximal phalanx base osteotomy. Normal values for this angle range between 0–8°.

The Tangential Angle to the Second (TASA) Application is formed by a line representing the effective articular cartilage at the $1^{st}$ metatarsal head and a line perpendicular to the bisection of the second metatarsal. Normal values for this angle range between 0° (+/−5°).

The Intermetatarsal Angle (IM) is derived from measurement of the 1st and 2nd metatarsal bisections and the angle they form represents the degree of $1^{st}$ metatarsal angulation in a forefoot deformity and is one of the most important assessments when choosing the appropriate surgical procedure. Normal values for this angle range between 0–12°.

The Relative Intermetatarsal Angle (RIM) utilizes a bisection of the 1st metatarsal head to determine the $1^{st}$ metatarsal axis which is then compared to the $2^{nd}$ metatarsal axis. This technique allows for evaluation of $1^{st}$ metatarsal bowing and, most importantly, the determination of the corrected IM angle following a head osteotomy procedure. Normal values for this angle range between 0–8°.

The "True" Intermetatarsal Angle (IMA) takes into account the metatarsus adductus angle and more correctly assesses the 1st ray structural deformity as it relates to the foot. The following equation illustrates how this angle is measured:

$$IMA_t = IMA + (MAA - \text{Normal } 15°)$$

Normal values for this angle range between 0–8°.

The Intermetatarsal Cortical Angle takes into account the IM angle at the cortical bases of the $1^{st}$ and $2^{nd}$ metatarsals. This information can be utilized to determine if a majority of the deformity originates at the base of the $1^{st}$ metatarsal.

The Metatarsus Adductus Angle (MAA) measures the relationship of the longitudinal axis of the lesser tarsus with that of the metatarsus (second metatarsal). The lesser tarsus axis is determined by connecting the midpoint between the medial aspect of the $1^{st}$ met-cuneiform and talo-navicular joints with the midpoint between the lateral aspect of the calcaneal-cuboid joint and the $4^{th}$ metatarsal-cuboid joint. This measurement is critical in determining the foot type and the significance of other measurements such as IM and HAA. Normal values for this angle is <15°=rectus foot type–normal.

Engle's Angle represents the comparison of the $2^{nd}$ metatarsal bisection with the bisection of the intermediate cuneiform. This measurement allows for a quick estimation of the Metatarsus Adductus Angle. Normal value for this angle is <18°.

The Metatarsal Break Angle (MBA) is formed by the tangential line across the tips of the $1^{st}$ and $2^{nd}$ metatarsal heads and a tangential line drawn across the tips of the $2^{nd}$ and $5^{th}$ metatarsal heads. The resultant angle represents the linear relation of the metatarsal head parabola and helps assess abnormal metatarsal length. This assessment also allows for quantification of how much shortening or lengthening of the $1^{st}$ metatarsal is available when planning osteotomies. Normal value for this angle is 140°.

The $1^{st}$ Metatarsal-Phalangeal Joint Position assesses the congruency of the $1^{st}$ MPJ using the existing lines representing the articular surfaces at the joint. Based on the relationship of these lines, the joint is classified as congruous (normal), deviated, or subluxed. This measurement is valuable in determining the amount of soft tissue balancing that is needed. Also, depending on the values for PASA, DASA and HAA, this measurement will aid in determining if a deformity is structural, positional or a combination of both. Normal value for this angle is 0° (parallel) to angulated 3°.

The Tibial Sesamoid Position (TSP) describes the position of the tibial sesamoid in relation to the bisection of the $1^{st}$ metatarsal by assigning a numerical sequence (1–7) with higher numbers indicating increasing lateral deviation. Positions of the sesamoid are defined as follows: TSP1=lateral to bisection. TSP2=lateral border touching bisection, TSP3=up to ½ of it lateral to the bisection, TSP4=equally divided by the bisection, TSP5=greater than half is lateral to bisection, TSP6=medial border touching the bisection, and TSP7=entirely lateral to the bisection. TSP is useful in evaluating the progression of an HAV deformity and in determining the extent of lateral soft tissue release needed. A reduction in the RIM angle should lead to a reduction in the TSP. Normal values are TSP 1–3.

The Relative Tibial Sesamoid Position (R-TSP) is determined the same way as described above except the head bisection is used instead of the more proximal bisection traditionally used when determining the bisection line of the $1^{st}$ metatarsal. This revision of the traditional TSP is useful following an osteotomy of the $1^{st}$ metatarsal head. The R-TSP gives a more accurate indication of the corrected sesamoid position by considering the revised position of the median crista relative to the tibial sesamoid position. Normal values are RTSP 1–3.

Metatarsal Protrusion Distance (MPD) is a comparison of the $1^{st}$ & $2^{nd}$ relative metatarsal lengths. The value is determined by utilizing the intersection of the previously drawn bisections of the $1^{st}$ & $2^{nd}$ metatarsals as the center of a circle with the radius extending to the most distal aspect of the 1st metatarsal. The MPD is then calculated based on subtracting the distance the distal aspect of the $2^{nd}$ metatarsal is from the arc of this circle from the value of its radius. When the $1^{st}$ metatarsal is longer, this value will be positive and when the $2^{nd}$ metatarsal is longer, the MPD will be negative. Normal value for this distance is +/−2 mm.

The $1^{st}$ Metatarsal Deformation Angle is formed when an angular deformity exists in the $1^{st}$ metatarsal. One line is formed by bisecting the base and the other is formed by the normal bisection of the shaft of the $1^{st}$ metatarsal. Theoretically, this angle is expected to be 0° or very close to 0°, thus indicating a straight $1^{st}$ metatarsal. This angle is included to help determine the origin of angular deformity in the $1^{st}$ ray. Normal value for this angle is 0°.

The $1^{st}$ Metatarsal-Medial Cuneiform Angle is formed by a line perpendicular to the bisection of the $1^{st}$ metatarsal and a second line that is perpendicular to the bisection of the medical cuneiform. If the value of this angle is greater than 25°, correction of a high IM angle can be considered more proximally on the $1^{st}$ metatarsal. Normal values for this angle range from 0–25°.

The Metatarsus Varus Angle (MVA) is formed by the bisection of the $1^{st}$ metatarsal and the bisection of the medial cuneiform. This measurement helps determine the origin of an abnormally high IM angle and aid in choosing the location to correct such a deformity. This angle has also been referred to as the $1^{st}$ metatarsocuneiform joint angle. Normal values for this angle range from 0–25°.

The $1^{st}$ Metatarsocuneiform Angle and its Relation to the $2^{nd}$ Metatarsal is formed by the line perpendicular to the bisection of the $2^{nd}$ metatarsal and a line parallel to the articular surface of the $1^{st}$ metatarsal base. The original authors of this measurement demonstrated the positive relationship between the high intermetatarsal angle and this angle. This measurement only aids in the evaluation of a high IM angle and its etiology. If a high value is found with this measurement, the practitioner may wish to select a basal osteotomy to reduce the IM.

The Metatarsal Head Split Distance Application is determined by the distance between the most lateral aspect of the $1^{st}$ metatarsal head and the adjacent most medial aspect of the $2^{nd}$ metatarsal head. The benefit of this measurement involves quantifying the amount of lateral transverse $1^{st}$ metatarsal head displacement following an IM reducing osteotomy. This measurement is also useful preoperatively to determine the amount of space between the $1^{st}$ and $2^{nd}$ metatarsal heads. Normal values range between 6–7 mm.

Metatarsal Base Split Distance refers to the distance between adjacent points of the $1^{st}$ and $2^{nd}$ metatarsal bases. An increase in this value may indicate a component of an increase in IM that may be positional in nature and caused by retrograde forces of the HAV deformity. Normal value for this angle is <2 mm.

The Forefoot Width quantifies the actual width of the forefoot based on its most medial and lateral bony landmarks. The distance is measured from the most medial aspect of the $1^{st}$ metatarsal head to the most lateral aspect of the $5^{th}$ metatarsal head. This measurement provides important information about a possible splayfoot deformity and is useful for preoperative planning and postoperative assessment of the forefoot width reduction. Normal values range from 7.0 to 9.0 cm.

The Tibial Sesamoid $2^{nd}$ Metatarsal Distance is a structural relationship that is measured in mm from the medial border of the tibial sesamoid to the bisection of the $2^{nd}$ metatarsal. Because this relationship is fixed, it can be used to verify the sesamoid apparatus is remains firmly fixed despite a forefoot deformity or prior 1$^{st}$ metatarsal osteotomy. No normal is applicable.

Figure 13:
FIG. 13 is a diagram illustrating Tailor's Bunion measurements.
Figure 15:
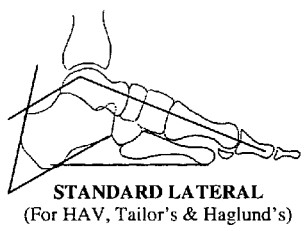
FIG. 15 is a diagram illustrating Standard Lateral measurements.
Figure 17:
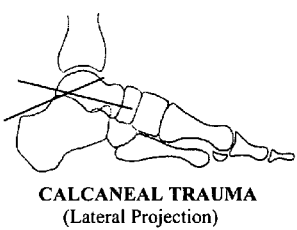
FIG. 17 is a diagram illustrating Calcaneal Trauma measurements.
Figure 21:
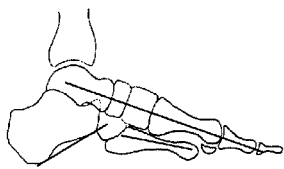
FIG. 21 is a diagram illustrating Biomechanical (Lateral Projection) measurements.

Those skilled in the art will appreciate that the present invention can be used to evaluate a myriad of other evaluations. FIGS. 12 and 13 provide a landmark key and description of measurements for a Tailor's Bunion evaluation. FIGS. 14 and 15 provide similar information for a Standard Lateral evaluation, which is useful for HAV, Tailor's and Haglund's. Landmark and measurement information is set forth in FIGS. 16 and 17 for a Calcaneal Trauma evaluation. FIGS. 18 and 19 provide landmarks and measurements for a Biomechanical evaluation (AP projection), and FIGS. 20 and 21 are provided for a Biomechanical evaluation (lateral projection). Application of the various measurements for these evaluations will now be further described.

Respecting the Tailor's Bunion Evaluation (AP Projection)(see FIGS. 12, 13), the 4th–5th Intermetatarsal Angle (Traditional) angle is formed by lines which bisect the 4th and 5th metatarsals. The value obtained here will quantify the magnitude of 5th metatarsal lateral drift and aid in determining at what level a corrective osteotomy should be made. A splayfoot deformity is determined when this angle is greater than 8° and the 1st Intermetatarsal Angle is greater than 12°. Normal value for this angle is <8°.

The 4th and 5th Intermetatarsal Angle (Fallat & Buckholz) is created by a line drawn adjacent and parallel to the 5th metatarsal shaft and a line that bisects the 4th metatarsal. Normal value for this angle is ≦6.47°.

The 2nd and 5th Intermetatarsal Angle is determined by lines that bisect the 2nd and 5th metatarsals and assesses the width of the lateral forefoot. Normal value for this angle is 16°+/−2°.

The 1st Intermetatarsal Angle (IM) is formed by the lines bisecting the 1st and 2nd metatarsals. Generally, this angle is increased in patients with tailor's bunions because of the high correction of HAV with tailor's bunions. Splayfoot is determined when the 1st Intermetatarsal angle is greater than 12° and the 4th and 5th Intermetatarsal angle is greater than 8°. Normal values for this angle range between 0–12°.

The Forefoot Width quantifies the actual width of the forefoot based on the most medial and lateral bony landmarks. The distance is measured from the most medial aspect of the 1st metatarsal head to the most lateral aspect of the 5th metatarsal head. This measurement provides additional information regarding a possible splayfoot deformity and allows the surgeon to quantify a decrease forefoot width following a corrective osteotomy for a tailor's bunion deformity. Normal values for this angle range between 7.0 to 9.0 cm.

The 5th Metatarsal Lateral Deviation Angle is formed by a line that bisects the head and neck of the 5th metatarsal and a line that is drawn parallel to the medial surface of the 5th metatarsal. Lateral bowing is considered to be a structural problem within the 5th metatarsal where the distal third of the shaft is deviated laterally. When present, this deformity is significant and should be assessed when planning corrective procedures. Normal value of this angle is <2.64°.

The Metatarsal Break Angle is formed by the tangential line across the tips of the 1st and 2nd metatarsal heads and a tangential line drawn across the tips of the 2nd and 5th metatarsal heads. The resultant angle represents the linear relation of the metatarsal head parabola. This helps assess abnormal metatarsal length and aids in planning shortening or lengthening osteotomies. Normal value of this angle is 140°.

Respecting the Standard Lateral evaluation (Lateral Projection)(see FIGS. 14, 15), the Calcaneal Inclination Angle is formed by a line connecting the plantar aspect of the calcaneus and the 5th metatarsal head (plane of support) and a line tangent to the anterior tubercle and plantar tuberosity of the calcaneus. This angle will decrease in a pronated foot and a flatfoot deformity and will increase in a supinated foot and cavus foot deformity. Normal range for this angle is 21°+/−3°.

The Talar Declination Angle is formed by the line connecting the plantar aspect of the 5th metatarsal head with the plantar tuberosity of the calcaneus and a line bisecting the head and neck of the talus. This angle will increase with STJ pronation and decrease with STJ supination. Normal value for this angle is 210.

The Lateral Talo-calcaneal Angle is an estimation of the amount of divergence between the talus and calcaneous and is formed by the line bisecting the talar head an neck along with the line tangent to the anterior tubercle and plantar tuberosity of the calcaneus. This angle will increase with STJ pronation and decrease with STJ supination. Normal values for this angle fall between 40–50°.

The 1st Metatarsal Declination Angle is formed by the line representing the plan of support and the bisection of the 1st metatarsal. This is a positional and structural angle that will decrease with STJ pronation and increase with STJ supination. This angle is also useful for post-operative evaluation of any sagittal plane changes in the 1st metatarsal. Normal value of this angle is 20°.

The Lateral Talo-1st Metatarsal Angle is formed by the line bisecting the talar head and neck and a line bisecting the shaft of the 1st metatarsal. Ideally, these lines should be overlapping and nearly parallel, thus indicating stability in the 1st ray. Normal value for this range is +4° to −4°.

The Fowler-Philip Angle is formed between a line tangent to the anterior tubercle and the plantar tuberosity of the calcaneous and a line tangent to the posterior prominence at the insertion of the achilles tendon. Fowler and Philip stated that any value greater than or equal to 75° may be consistent with a Haglund's Deformity. Normal values for this angle range from 44–69°.

The Total Angle is determined by combining the Calcaneal Inclination Angle with the Fowler-Phillip angle. Ruch introduced this method for evaluating the possibility of a Haglund's Deformity because it more accurately measured the presence of an abnormal retrocalcaneal enlargement outside of normal anatomy. Normal value of this angle is <92°.

The Parallel Pitch Lines Angle constructed by drawing a line tangent to the plantar tuberosity and the anterior tubercle of the calcaneus (PPL1). Then a line perpendicular to this line is drawn through the posterior superior aspect of the posterior facet. At this point on the facet a 3rd line (PPL2) is drawn parallel to PPL1. The relationship of a posterior bursal projection with the PPL2 will aid in determining the presence of a Hagland's Deformity. Normal value is a bursal projection touching or below PPL2(−).

Respecting the Calcaneal Trauma Evaluation (Lateral Projection)(see FIGS. 16, 17), the Bohler's Angle is created by a line connecting the posterior-superior aspect of the posterior facet and the anterior process of the calcaneus and a line connecting the posterior-superior aspect of the posterior facet with the most superior portion of the posterior calcaneal tuberosity. Bohler's Angle is primarily used to determine the amount of intra-articular depression of the calcaneus. Also, this angle is more acute in pes cavus deformities and in children's feet, but is flatter in pes valgus deformities. Normal values for this angle range between 25–40°.

The Gissane's Crucial Angle is created by the subchondral bone of the posterior facet and the subchondral bone of the anterior and middle facets. The bone creating this angle supports the lateral process of the talus and indicates the degree of talar depression into the calcaneus. Normal values for this angle range between 120–145°.

The Posterior Facet Angle of Inclination determines the angle the posterior facet of the calcaneus makes with the plane support. This measurement is useful in determining the involvement of the posterior facet pre-operatively and assess the reconstruction post-operatively. Normal value for this angle is 45°+/−5°.

The Calcaneal Inclination Angle is formed by the line connecting the plantar tuberosity of the calcaneus with the most anterior-plantar aspect of the calcaneus and a line representing the plane of support. This angle will help establish the angular relationship of the calcaneus to the forefoot for both pre-operative and post-reduction comparison. Normal value for this angle is 21°+/−3°.

The Calcaneal Compression Angle is formed by the line tangent to the posterior-superior aspect of the calcaneal posterior facet and the anterior process of the calcaneus and a line connecting the plantar tuberosity of the calcaneus with the most anterior-plantar aspect of the calcaneus. This angle aids in evaluation of the pre- and post-reduction results of depression type calcaneal fractures. Normal values of this angle are used for comparison to contralateral foot and post-operatively.

Respecting the Biomechanical evaluation (AP Projection) (see FIGS. 18, 19), the Hallux Abductus Angle (HAA) is formed by the bisections of the proximal phalanx of the hallux and the 1st metatarsal. Although this angle does not directly represent biomechanical abnormalities, due to reactive forces from a high Intermetatarsal Angle, Metatarsus Adductus Deformity, or a foot that overly pronates, this angle may be increased. Normal values for this angle range between 0–15°.

The Intermetatarsal Angle (IM) is formed by the bisection of the 1st metatarsal and the bisection of the second metatarsal and it is an estimation of the medial deviation of the 1st metatarsal. This mostly structural angle increases with the lack of stability of the 1st ray. Normal value for this angle ranges between 0–12°.

The "True" Intermetatarsal Angle ($IMA_t$) takes into account the metatarsus adductus angle and correctly assesses this 1st ray deformity as it relates to the foot. The following equation illustrates how this angle is measured:

$$IMA_t = IMA + (MAA - \text{Normal } 15°)$$

Normal values for this angle range between 0–8°.

The Metarsus Adductus Angle (MAA) measures the relationship of the longitudinal axis of the lesser tarsus with that of the metatarsus. The lesser tarsus axis is determined by connecting the midpoint between the medial aspect of the 1st metatarsocuneiform and talongavicular joints with the midpoint and the 4th metatarsal-cuboid joint. This measurement is critical in determining the foot type and significance of other measurements.

Engle's Angle represents the comparison of the $2^{nd}$ metatarsal bisection with the bisection of the intermediate cuneiform. This measurement allows for a quick estimation of the Metatarsus Adductus Angle. Normal value for this angle is <18°.

The Forefoot Width quantifies the actual width of the forefoot based on its most medial and lateral bony landmarks. The distance is measured from the most medial aspect of the $1^{st}$ metatarsal head to the most lateral aspect of the $5^{th}$ metatarsal head. This measurement provides important information about a possible splayfoot deformity. Normal values range from 7.0 to 9.0 cm.

The Tibial Sesamoid Position (TSP) describes the position of the tibial sesamoid in relation to the bisection of the $1^{st}$ metatarsal by assigning a numerical sequence (1–7) with higher numbers indicating increasing lateral deviation. Positions of the sesamoid are defined as follows: TSP1=lateral to bisection. TSP2=lateral border touching bisection, TSP3=up to ½ of it lateral to the bisection, TSP4=equally divided by the bisection, TSP5=greater than half is lateral to bisection, TSP6=medial border touching the bisection, and TSP7=entirely lateral to the bisection. TSP is useful in evaluating the progression of an HAV deformity and in determining the extent of lateral soft tissue release needed. Normal values for this position are TSP 1–3.

The Tibial Sesamoid $2^{nd}$ Metatarsal Distance is a structural relationship that is measured in mm from the medial border of the tibial sesamoid to the bisection of the $2^{nd}$ metatarsal. Because this relationship is fixed, it can be used to verify the sesamoid apparatus is remains firmly fixed despite a forefoot deformity or prior $1^{st}$ metatarsal osteotomy. No normal is applicable.

The Metatarsal Protrusion Distance (MPD) is a comparison of the $1^{st}$ & $2^{nd}$ relative metatarsal lengths. The value is determined by utilizing the intersection of the previously drawn bisections of the $1^{st}$ & $2^{nd}$ metatarsals as the center of a circle with the radius extending to the most distal aspect of the 1st metatarsal. The MPD is then calculated based on subtracting the distance the distal aspect of the $2^{nd}$ metatarsal is from the arc of this circle from the value of its radius. When the $1^{st}$ metatarsal is longer, this value will be positive and when the $2^{nd}$ metatarsal is longer, the MPD will be negative. Normal value for this distance is between + or −2 mm.

The Cuboid Abduction Angle is formed by the lines tangent to the lateral border of the cuboid and the calcaneus. This value estimates the amount of abduction of the midfoot on the rearfoot and mirrors the lesser tarsus abductus angle. This positional angle increases with STJ pronation and abduction of the forefoot and midfoot. With supination of the STJ and adduction of the forefoot and midfoot, the cuboid adducts, decreasing the angle. Normal value for this angle ranges between 0–5°.

The Forefoot Adductus Angle is formed by the bisection of the 2nd metatarsal and the longitudinal bisection of the rearfoot. This is a positional angle that will decrease with pronation and decrease with supination. The normal value is undetermined. Normal values for this angle range between 0–14°.

The Percent of Talus-Navicular Articulation Angle assesses the amount the head of the talus articulates with the navicular. This measurement is positional and a decrease in articulation is noted with STJ pronation and adduction of the talus. With supination of the STJ and abduction of the talus, the percentage of talar head articulation increases. Normal value for this angle is ≧75% articulation of the talus with the navicular.

The Talo-calcaneal Angle (Kite's Angle) is formed by the bisection of the head and neck of the talus and the longitudinal axis of the calcaneus. This is a positional angle that measures the divergence of the calcaneus and talus. With STJ pronation this angle increases, whereas with STJ supination, the angle will decrease. Normal value of this angle is 18°.

The Lesser Tarsus Angle is measured by the longitudinal bisection of the tarsus and the longitudinal bisection of the tarsus. This positional angle will increase with STJ pronation and decrease with STJ supination.

The 1st Metatarsal Calcaneal Angle is an assessment of the relationship of the 1st metatarsal to the rearfoot in a compensated position. Both the structural metatarsus adductus angle and the positional forefoot adductus angles are accounted for in this measurement. This angle decreases the STJ pronation and increases with STJ supination.

Respecting the Biomechanical evaluation (Lateral Projection)(see FIGS. 20, 21), the Calcaneal Inclination Angle This estimation in the pitch of the calcaneus is measured by the line extending from the proximal plantar surface of the calcaneus to the anterior inferior surface of the calcaneus and a line representing the supporting surface. Primarily a structural angle, STJ pronation may lead to some decrease whereas supination may increase the angle slightly. Severe decreases are noted in pes planus deformities whereas pes cavus feet will have a high CIA. Normal value for this angle is 21°+/−3°.

The Talar Declination Angle is formed by the line connecting the plantar aspect of the 5th metatarsal head with the plantar tuberosity of the calcaneus and a line bisecting the head and neck of the talus. This angle will increase with STJ pronation and decrease with STJ supination. Normal value for this angle is 21°.

The Lateral Talo-calcaneal Angle is an estimation of the amount of divergence between the talus and calcaneous and is formed by the line bisecting the talar head an neck along with the line tangent to the anterior tubercle and plantar tuberosity of the calcaneus. This angle will increase with STJ pronation and decrease with STJ supination. Normal value range of this angle is 40–50°.

The 1st Metatarsal Declination Angle is formed by the line representing the plan of support and the bisection of the 1st metatarsal. This is a positional and structural angle that will decrease with STJ pronation and increase with STJ supination. This angle is also useful for post-operative evaluation of any sagittal plane changes in the 1st metatarsal. Normal value of this angle is 20°.

The Seiberg Index measures the perpendicular distance from the dorsum of the 1st and 2nd metatarsals at the proximal and distal aspects. The proximal measurement is subtracted from the distal to obtain the Seiberg Index. Metatarsus primus elevatus will produce a positive value whereas a plantarly declinated 1st ray will produce a negative Index. Normal value for this index is 0 mm.

The Lateral Talo-1st Metatarsal Angle is formed by the line bisecting the talar head and neck and a line bisecting the shaft of the 1st metatarsal. Ideally, these lines should be overlapping and nearly parallel, thus indicating stability in the 1st ray. Normal values for this angle fall in the range +4° to −4°.

The 5th Metatarsal Declination Angle is formed by the line bisecting the 5th metatarsal and the line representing the weight bearing surface. With pronation, this angle increases as weight is shifted more to the medial column, whereas supination will cause this angle to decrease as the foot is rolled more onto the lateral column. Normal value for this angle is ≦10°.

The Height of the Navicular Angle is the distance of the plantarmost aspect of the navicular to the plane of support. This distance is greater in pes cavus and with supination and decreased in pes planus and eversion of the midfoot with excessive midtarsal pronation.

Those skilled in the art will appreciate that the present invention can be used to evaluate numerous other conditions, including ankle injury and pediatric foot deformity. The steps of defining and identifying a set of applicable landmarks, as described previously, can be applied to these conditions as well.

A general description of the present invention as well as a preferred embodiment of the present invention has been set forth above. Those skilled in the art to which the present invention pertains will recognize and be able to practice additional variations in the methods and systems described which fall within the teachings of this invention. Accordingly, all such modifications and additions are deemed to be within the scope of the invention which is to be limited only by claims appended hereto.

What is claimed is:

1. A first ever digital system for evaluating foot and ankle radiographs having the advantage of providing accurate measurement information based upon selected landmarks on the radiograph, the system comprising:
   a computing device including a digital storage medium and a central processing unit;
   a coordinate generating backlighted digitizing device operatively connected to the computing device for generating coordinate data for the selected landmarks on the radiograph; and
   software in the digital storage medium executable by the computing device for converting the coordinate data into clinically descriptive measurement information.

2. The system of claim 1 further comprising a a database connected to the computing device that includes patient data related to one or more patients.

3. The system of claim 2 wherein the patient data includes information quantifying osseous relationships on the radiographs.

4. The system of claim 1 wherein the digitizing device includes a cursor for selecting the landmark to digitize.

5. The system of claim 1 wherein the clinically descriptive measurement information includes angles quantifying osseous relationships.

6. The system of claim 5 wherein the software provides normal values for comparison with the clinically descriptive measurement information.

7. The system of claim 1 wherein the clinically descriptive measurement information includes distances quantifying osseous relationships.

8. The system of claim 7 wherein the software provides normal values for comparison with the clinically descriptive measurement information.

9. A software article for use in evaluating foot and ankle radiographs that provides accurate measurement information based upon selected landmarks on the radiograph, the article comprising:
   a computer-readable signal-bearing medium;
   means in the medium for determining landmarks on the radiograph to be located;
   means in the medium for reading coordinate data for the landmarks; and
   means in the medium for converting the coordinate data into clinically descriptive measurement information.

10. The article of claim 9 further comprising a means in the medium for returning the clinically descriptive measurement information in a table format with normal values for comparison.

11. The article of claim 9 further comprising a means in the medium for returning the clinically descriptive information as a graphical illustration of the landmarks with lines drawn identifying angular osseous relationships.

12. The article of claim 9 wherein the medium is a recordable data storage medium.

13. The article of claim 9 wherein the medium is a modulated carrier signal.

14. The article of claim 13 wherein the signal is a transmission over a global computer network.

15. The article of claim 13 wherein the signal is a transmission over a wireless network.

16. A method of analyzing foot and ankle radiographs that minimizes the time required to perform the analysis and provides accurate measurement information, the method comprising:
    providing a computing device including a digital storage medium and a central processing unit, a coordinate generating backlighted digitizing device operatively connected to the computing device for generating coordinate data from the radiograph, and software in the digital storage medium executable by the computing device for converting the coordinate data into clinically descriptive measurement information;
    selecting landmarks on the radiograph for evaluating a medical condition;
    digitizing points on the radiograph corresponding to the landmarks through use of the digitizing device; and
    reviewing the clinically descriptive measurement information determined by the software.

17. The method of claim 16 further comprising the step of comparing the clinically descriptive measurement information with corresponding normal values.

18. The method of claim 16 wherein the medical condition is HAV.

19. The method of claim 16 wherein the medical condition is Tailor's bunion condition.

20. The method of claim 16 wherein the medical condition is Haglund's condition.

21. The method of claim 16 wherein the medical condition is a biomechanical deformity.

22. The method of claim 16 wherein the medical condition is a calcaneus traumatic injury.

23. The method of claim 16 wherein the medical condition is a pediatric foot deformity.

24. The method of claim 16 wherein the medical condition is an ankle traumatic injury.

25. A method of analyzing foot and ankle radiographs for a patient that minimizes the time required to perform the analysis and provides accurate measurement information, the method comprising:
    selecting a medical condition for evaluation;
    selecting a radiograph of the patient corresponding to the medical condition;
    determining landmarks to be located on the radiograph for evaluation of the medical condition;
    digitizing points for the landmarks as coordinate data on a backlighted digitizer;
    converting the coordinate data into clinical measurement information; and
    displaying the clinical measurement information.

26. The method of claim 25 further comprising the step of displaying normal values corresponding to the clinical measurement information for comparison.

27. The method of claim 25 further comprising the step of storing the clinical measurement information for the patient in a database.

28. A method of analyzing foot and ankle radiographs for a patient that minimizes the time required to perform the analysis and provides accurate measurement information, the method comprising:
    selecting a medical condition for evaluation;
    defining a plurality of landmarks for use with the medical condition;
    selecting a radiograph of the patient corresponding to the plurality of landmarks;
    identifying the plurality of landmarks on the radiograph; digitizing the identified landmarks as coordinate data on a backlighted digitizer;
    converting the coordinate data into clinical measurement information; and
    displaying the clinical measurement information.

29. The method of claim 28 wherein the medical condition is HAV.

30. The method of claim 28 wherein the medical condition is Tailor's bunion condition.

31. The method of claim 28 wherein the medical condition is Haglund's condition.

32. The method of claim 28 wherein the medical condition is a biomechanical deformity.

33. The method of claim 28 wherein the medical condition is a calcaneus traumatic injury.

34. The method of claim 28 wherein the medical condition is an ankle traumatic injury.

35. The method of claim 28 wherein the medical condition is a pediatric foot deformity.

* * * * *